United States Patent
Dunham

(10) Patent No.: US 11,725,305 B2
(45) Date of Patent: Aug. 15, 2023

(54) RAPID LIBRARY CONSTRUCTION FOR HIGH THROUGHPUT SEQUENCING

(71) Applicant: SEQONCE BIOSCIENCES, INC., Pasadena, CA (US)

(72) Inventor: Joseph Dunham, El Segundo, CA (US)

(73) Assignee: SEQONCE BIOSCIENCES, INC., Pasadena, CA (US)

( * ) Notice: Subject to any disclaimer, the term of this patent is extended or adjusted under 35 U.S.C. 154(b) by 614 days.

(21) Appl. No.: 16/631,321

(22) PCT Filed: Jul. 17, 2018

(86) PCT No.: PCT/US2018/042500
§ 371 (c)(1),
(2) Date: Jan. 15, 2020

(87) PCT Pub. No.: WO2019/018404
PCT Pub. Date: Jan. 24, 2019

(65) Prior Publication Data
US 2020/0208299 A1    Jul. 2, 2020

Related U.S. Application Data

(60) Provisional application No. 62/533,483, filed on Jul. 17, 2017.

(51) Int. Cl.
| | | |
|---|---|---|
| C40B 50/06 | (2006.01) | |
| C12N 15/10 | (2006.01) | |
| C40B 70/00 | (2006.01) | |
| C40B 80/00 | (2006.01) | |

(52) U.S. Cl.
CPC .......... *C40B 50/06* (2013.01); *C12N 15/1068* (2013.01); *C40B 70/00* (2013.01); *C40B 80/00* (2013.01)

(58) Field of Classification Search
None
See application file for complete search history.

(56) References Cited

U.S. PATENT DOCUMENTS

| | | |
|---|---|---|
| 6,440,943 B1 | 8/2002 | Cook et al. |
| 2003/0143599 A1 | 7/2003 | Makarov et al. |
| 2013/0116130 A1 | 5/2013 | Fu et al. |
| 2015/0119261 A1 | 4/2015 | Richard |
| 2016/0083724 A1* | 3/2016 | Dunham ............ C12N 15/1093 506/4 |
| 2016/0208240 A1 | 7/2016 | Zhang et al. |

OTHER PUBLICATIONS

International Search Report and Written Opinion in International Application No. PCT/US2018/042500, dated Sep. 25, 2018.
International Preliminary Report on Patentability in International Application No. PCT/US2018/042500, dated Jan. 30, 2020.
Ouick et al., "Multiplex PCR method for MinION and Illumina sequencing of Zika and other virus genomes directly from clinical samples", Nat. Protoc. 2017, 12(6); 1261-1276.

* cited by examiner

*Primary Examiner* — Kaijiang Zhang
(74) *Attorney, Agent, or Firm* — Raphael Bellum PLLC

(57) ABSTRACT

Rapid methods, capable of being performed in a single reaction tube, are described herein for constructing libraries for high-throughput polynucleotide sequencing applications, such as next generation sequencing (NGS) applications. Oligonucleotide probes include chemically-active groups at their 5' or 3' ends, or both, to facilitate the cleavage of their 5' or 3' ends, or both, following their hybridization to the single-stranded ends of frayed template fragments. Cleavage of probe ends reveal single-stranded regions at the ends of the hybridized fragments. Adaptors, specific to these ends, are ligated to the hybridized probe/template fragments, and blunt end fragments are ligated to blunt ends of hybridized probe/template fragments, if present, to generate the adaptor-ligated fragments of the library.

20 Claims, 14 Drawing Sheets

Rapid DNA-seq

Fragmentation

Novel Library Construction

PCR (optional)

20-50 min

Key Features:
* Unique set of reactions
* 3 step protocol
* Single tube
* Less user hands on time
* Reduced user error
* Easy to automate
* Single bead cleanup after PCR.

RAPID LIBRARY CONSTRUCTION FOR HIGH THROUGHPUT SEQUENCING

FIELD OF THE INVENTION

The field of this invention relates to the construction of sequencing libraries for high throughput polynucleotide sequencing.

BACKGROUND

High throughput screening allows for the rapid determination of the nucleotide sequence of a DNA polymer by simultaneously detecting millions of molecules of DNA of a small size range (100-800 bp). The limitation of short read sequencing is that random fragmentation of genomic DNA into millions of very small fragments results in computational assembly errors, even by the best pipelines. Repetitive regions and complex rearrangements and duplications, large scale insertions or deletions are routinely falsely incorporated or absent. The most commonly used high throughput sequencing platforms are resource intensive, both in terms of time and reagents, which limits the capacity of existing sequencing methods, such as next generation sequencing (NGS) methods for de novo genome assembly and correct genome assignment of rearrangements and duplications or insertions, which are particularly prevalent in organisms with large genome sizes. However, by developing approaches for consolidating multiple steps of the construction of sequencing libraries into a single reaction tube, the time and reagent costs associated with high throughput sequencing methods can be significantly improved. Such improvements are described herein.

SUMMARY OF THE INVENTION

This invention relates to the construction of libraries for high-throughput nucleotide sequencing methods, such as next generation sequencing (NGS) applications. Libraries constructed according to methods of the invention contain sequencing adaptor-ligated duplexes of oligonucleotide probe-hybridized template sequence fragments. Probes of the invention may include a chemically-active group at their 5' or 3' ends, or both, to facilitate the cleavage of their 5' or 3' ends, or both, following their hybridization, to reveal single-stranded regions at the ends of the hybridized fragments. Adaptors, specific to these ends, are ligated to the hybridized probe/template fragments, and blunt end fragments are ligated to blunt ends of hybridized probe/template fragments, if present, to generate the adaptor-ligated fragments of the library. Methods of the invention for generating sequencing libraries can be performed in a single reaction tube with relatively few steps, and are ideal for incorporation into kits for preparing sequencing libraries.

DETAILED DESCRIPTION

Figure 1:
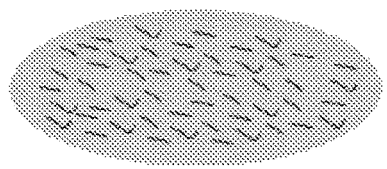
FIG. 1 shows a schematic of the construction of a library for NGS. Purified DNA is fragmented in less than 12 min. and is used directly for library construction. Library construction follows a unique approach for generating DNA ends derived from an original DNA template for adaptor ligation. Library construction takes less than 13 min. and can be directly used in a PCR reaction. No purification steps are required for the library construction, though a final bead purification step may be employed to clean up the preparation or size selection of library products after the PCR step. The simple three step protocol is performed in a single tube.
Figure 1:
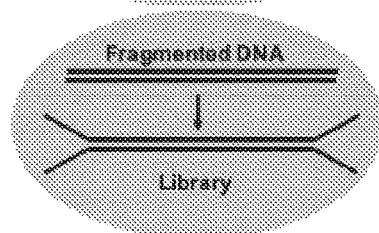
Figure 1:
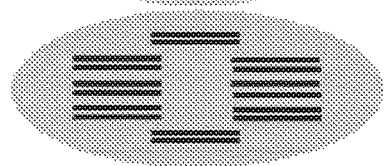

The invention is directed to the construction of libraries for high-throughput nucleotide sequencing. More particularly, methods of the invention generate adaptor-ligated libraries of nucleic acid fragments that can be used directly in high throughput sequencing methods, like, for example, next generation sequencing (NGS) applications, such as whole genome sequencing, whole genome bisulfite sequencing, targeted bisulfite sequencing, RNAseq, mRNAseq, ChiP-seq, multiplex PCR products, and library construction for hybrid-capture. In that regard, methods of the invention are disclosed herein for preparing adaptor-ligated duplexes of oligonucleotide probe-hybridized fragments of input polynucleotide templates. Oligonucleotide probes according to the invention comprise a chemically-active group at either, or both of, their 5' or 3' ends, which can be cleaved following their hybridization to frayed, single-stranded regions at the ends of the input fragments. The probes are, at least, equivalent in length to the single-stranded regions, and cleavage of the active group or groups results in the formation of single-stranded overhangs that can be annealed to a complementary overhang sequence of an adaptor, thereby ensuring correct and efficient ligations of adaptors to probe-hybridized fragments.

As stated above, a library according to the invention comprises fragments of input polynucleotides. The invention places no limits on the source or composition of input polynucleotide templates. For example, a library according to the invention can be generated from double- or single-stranded nucleic acids, including DNA or RNA derived from viral, bacterial, fungal and mammalian sources. Likewise, a library according to the invention can also be generated, for example, from genomic DNA, FFPE, cfDNA, cDNA or RNA:DNA hybrids, such as the product after generating the first strand of cDNA from RNA.

With respect to generating a library according to the invention from double-stranded input polynucleotides, input polynucleotides undergo a fragmentation. There is no particular limit to fragment sizes for use with a method according to the invention; however, it is expected most applications of a method according to the invention use fragments within a size distribution of from about 50 to 1000 base pairs (bp). The desired size range of fragments can be optimized depending upon user needs. For example, it may be desirable to generate a size distribution of fragments of 50-600 bp, with the majority of the fragment length distribution located between 100-400 bp. Alternatively, a size distribution of fragments of 300-1000 bp may be appropriate for other applications.

In general, polynucleotide fragments are randomly generated for use in the construction of a library according to the invention. Fragments are typically generated by enzymatic or ultrasonic fragmentation. For example, a plurality of input polynucleotides may be fragmented by an endonuclease, such as the enzyme that is commercially available as dsDNA Shearase™ Plus (Zymo Research), that cleaves phosphodiester bonds in DNA to yield oligonucleotide fragments with 5'-phosphate and 3'-hydroxyl termini. With respect to ultrasonic fragmentation, the use of a focused sonicator, such as a Covaris® Focused-ultrasonicator, may be used, for example, to generate a plurality of polynucleotide fragments for use in the construction of a library according to the invention. Irrespective of the approach used to generate fragments, however, fragmentation products can be used directly, without additional purification, in subsequent DNA fraying and probe hybridization steps of a method according to the invention.

Subsequent to obtaining double-stranded fragments of input template, a method according to the invention prepares the fragments for hybridization to oligonucleotide probes by a process referred to as "DNA Fraying", in which the Watson-Crick pairing of helix termini nucleotides is broken to produce single stranded DNA ends. These single-stranded ends can be represented as forming a double "V" structure (see FIG. 1). The fragmented template can be, for example, a frayed double stranded DNA, or a frayed RNA:DNA hybrid, such as the product after generating the first strand of cDNA from RNA. Various conditions can be used to promote the fraying process, including: the timed application of temperature; the use of additives, such as 1-9M urea, 1-99% formamide, ethylene carbonate; varying the concentrations of salts, including $MgCl_2$, NaCl, $NaH_2PO_4$, and $Na_2HPO_4$; or a combination thereof. The conditions used in the fraying process can be modified to generate a desired single-stranded region. As indicated, above, the desired length of the single-stranded regions that are generated by the fraying process correlate to the length(s) of the oligonucleotide probes in the particular probe pool to being used to generate a library according to the invention. Therefore, if a probe pool according to the invention contains probes that are from 1-6 nucleotides long, 6-15 nucleotides long, 15-50 nucleotides long, or any length from 1-50 nucleotides long, the desired lengths of single-stranded frayed ends will also be from 1-6 nucleotides long, 6-15 nucleotides long, 15-50 nucleotides long, or any length from 1-50 nucleotides long.

Oligonucleotide probes according to the invention can be composed of various common and exotic nucleotides, including, but not limited to, deoxynucleotides (dNTPs); dNTP/ribonucleotide triphosphates (rNTP) hybrids; peptide nucleic acids (PNA); locked nucleic acids (LNAs); isoguanosine (isoG); isocytosine (isoC); or any combination thereof. A probe according to the invention also comprises a cleavable chemically active group at the 3' or 5' ends, or both, of the oligonucleotide. More particularly, a "cleavable chemically active group" according to the invention can react with a "cleaving agent" to cleave away set numbers of nucleotides at the 3' or 5', or both ends of a probe according to the invention. This cleavage event creates a single stranded end of a probe/frayed-end duplex, that can be used to facilitate the efficient ligation of the duplex end to a double-stranded adaptor for use in a high throughput sequencing method, like next generation sequencing applications.

The cleavable chemically active group of a probe according to the invention can be located along the olignucleotide backbone of the probe. Examples of cleavable chemically active group include a modified 3'-5' internucleotide linkage in place of one of the phosphodiester groups, or a substituent on, or replacement of, one of the bases or sugars of the oligonucleotide. Alternatively, the cleavable chemically active group of a probe according to the invention can also be one or more of a dUTP, rATP, rCTP, rGTP, rUTP, isoG, isoC, a methylated nucleotide, an LNA, a PNA, or any combination thereof, at the 3' or 5' ends, or both, of a probe. Cleavable chemically-active groups according to the invention also include modifications of one or more nucleotides of an oligonucleotide probe by the addition of a PEG-spacer, an amino group, a biotin group, a maleimide compound, a phosphorothioate modification, or a phosphorylation modification. An oligonucleotide probe according to the invention may contain one or more phosphorothioate modifications, such as phosphorothioate bonds. For example, an oligonucleotide probe according to the invention can contain phosphorothioate modifications at one or more of the bases from bases 2-5 at the 3' or 5' ends, or both, of the probe.

A cleavable chemically-active group can be cleaved by chemical, thermal, or photolytic means. Alternatively, cleavable chemically-active group can be cleaved enzymatically, including, for example, uracil DNA glycosylase (UDG) or RNAse H, or restriction endonuclease activity if the cleavable chemically active group of an oligonucleotide probe according to the invention incorporates a restriction endonuclease site. Examples of restriction endonucleases for use in cleaving the chemically active group include BpmI, Bsgi, BseRI, BsmFI, and FokI.

Conditions for hybridizing probes to the single-stranded ends of frayed template fragments are generally dependent on the nucleotide composition of the probes. A typical approach for estimating the probe hybridization temperature for a method according to the invention is to calculate the minimal probe length with 100% GC content, and the longest probe length with 100% AT content for hybridization temperatures from about 40-70° C. Following the hybridization of probes to the single-stranded ends of target fragments, the ends of the resulting duplex complexes can be blunted by polymerase extension or polymerase exonuclease activity. After the ends of duplexes are blunted, 5', 3', or both, end cleavage of hybridized probes can proceed. Ligation of sequencing adaptors specific to these ends, as well as ligation of blunt end probes to blunt ends of the duplex, if present, can then occur.

An "adaptor" according to the method of the invention can refer to an oligonucleotide that may be attached to an overhang or blunt end of double-stranded duplex of a probe and end sequence of a template fragment. The composition of adaptor sequences can be, but is not limited to, polymers of DNA, RNA, PNA, or any combination thereof. An adaptor pool according to a method of the invention may include a first set of adaptors with a 3' overhang and a second set of adaptors with blunt ends. Conversely, an adaptor pool according to a method of the invention may include a first set of adaptors with a 5' overhang and a second set of adaptors with blunt ends, or an adaptor pool may include a first set of adaptors with a 3' overhang and a second set of adaptors with a 5' overhang.

Adaptor sequences may also contain, for example, priming sites, the complement of a priming site, recognition sites for endonucleases, common sequences and promoters. Adaptors may also incorporate modified nucleotides that modify the properties of the adaptor sequence. For example, phosphorothioate groups may be incorporated in one of the adaptor strands, such as an adaptor with a phosphorothioate modification on the last 1-3 3' bases at the 3' or 5', or both, ends.

A method according to the invention can also simplify the aforementioned fraying, probe hybridization, end blunting, cleavage, and ligation steps by performing all of the foregoing steps under the same buffer conditions, thereby saving significant time by allowing the consolidation of these steps into a single reaction tube. Indeed, the construction of a library using a method of the invention can be completed in about 30-40 minutes. Actual "hands-on" time can be as little as about 8 minutes, and the hybridization, partial exonuclease/extension, and cleavage/ligation steps can take only about 2, 3, and 9.5 minutes, respectively. An exemplary "single tube" reaction mixture for performing fraying, probe hybridization, and end blunting steps, according to the method of the invention includes Tris-HCl, $MgCl_2$, NaCl, bovine serum albumin (BSA), dithiothreitol (DTT), dNTPs, glycerol, and the random probe pool. For example, a preferred reaction mixture can include 10-20 mM Tris-HCl, 25-35 mM $MgCl_2$, 10-75 mM NaCl, 100 µg/ml bovine serum albumin (BSA), 1 mM dithiothreitol (DTT), 1-5 mM deoxyribonucleotide triphosphate (dNTP)s, 5-50% glycerol, and 20 mM random probe. Additions of the requisite enzymes to the same reaction tube can be sequential or simultaneous, and the reaction products can be used directly in a polymerase chain reaction (PCR).

Given the single tube simplicity of preparing a sequencing library, coupled with the lack of a required purification step, methods of library construction according the invention, as described above, are well-suited for their incoporation into a kit. For example, a kit can include: 1) a container, containing a pool of random probes that contain a cleavable 5' chemically active group, a 3' chemically active group, or both; 2) a pool of double-stranded truncated or full-length next generation sequencing adaptors; and 3) a separate container or containers, of a buffer or buffers, respectively, appropriate one or more of the following: (a) an enzymatic reaction to fray the ends of input polynucleotide fragments to expose single-stranded regions; (b) for hybridizing the probes to the single-stranded regions of the fragments; (c) an enzymatic reaction for blunting the ends of the probe/input fragment duplexes; (d) an enzymatic reaction cleaving the ends of probes, containing cleavable chemically active groups; (e) an enzymatic reaction ligating the sequencing adaptors to the double-stranded duplexes; and (f) an optional PCR reaction to amplify the library.

EXAMPLES

The following Examples describe the construction of next generation sequencing (NGS) libraries.

Example 1. Rapid Next Generation Sequencing Library Construction with Random Probes Containing a 5' Cleavable End High molecular weight DNA was purified by a commercial provider from three bacterial sources: 1) *Bordetella pertussis;* 2) *Escherichia coli*; and, 3) *Clostridium difficile*. Fifty nanograms of DNA from each purified source was subjected to random enzymatic fragmentation or ultra-focused sonication.

Figure 2A:
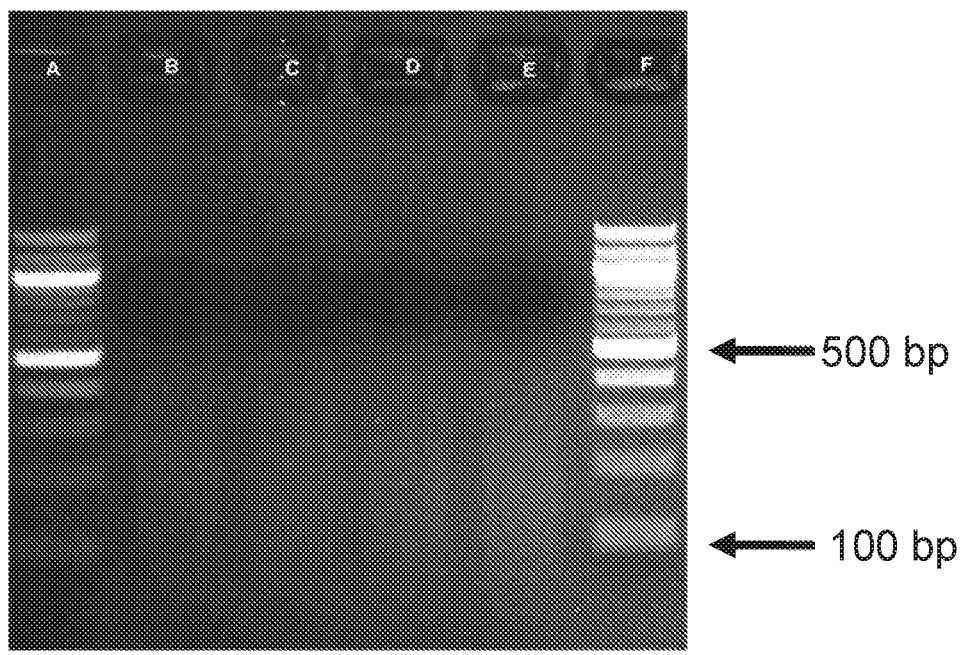
FIG. 2A shows DNA fragmentation time optimization at 37° C. Fifty ng of high molecular weight purified *E. coli* DNA was used for enzymatic reaction incubation times of: 5 min. (Lane B); 5.5 min. (Lane C); 6 min. (Lane D); 6.5 min. (Lane E). Fragmentation products were run on a 2% TBE agarose gel with a 100 bp ladder (Lane A).
Figure 2B:
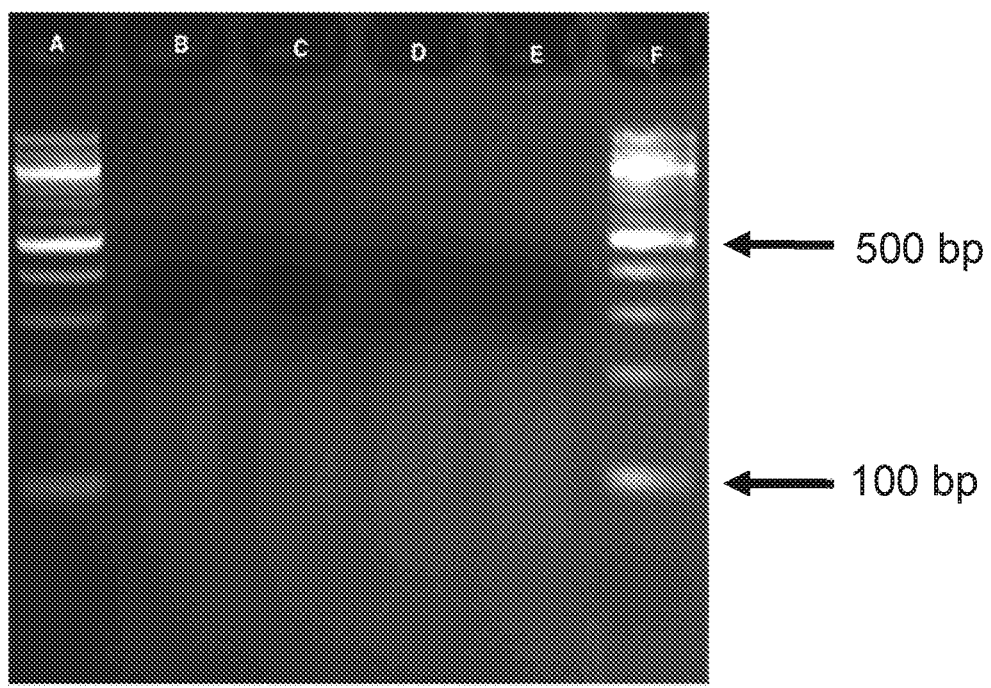
FIG. 2B shows DNA fragmentation time optimization at 37° C. Fifty ng of high molecular weight purified *E. coli* DNA was used for enzymatic reaction incubation times of: 6.5 min. (Lane B); 6.75 min. (Lane C); 7 min. (Lane D); 7.25 min. (Lane E). Fragmentation products were run on a 2% TBE agarose gel with a 100 bp ladder (Lane A).
Figure 2C:
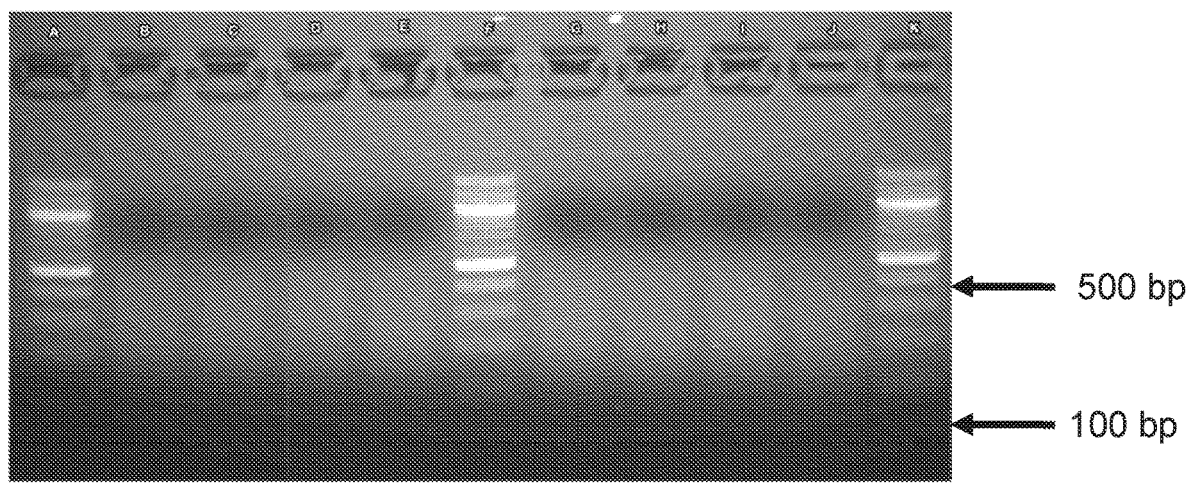
FIG. 2C shows DNA fragmentation time optimization at 42° C. for 3 and 4 minutes. Fifty ng of high molecular weight purified *E. coli* DNA was used for enzymatic reaction incubation times of: 3 min. (Lanes B and C) or 4 min. (Lanes G and H) in 0.1 mM EDTA; or 3 min. (Lanes D and E) or 4 min. (Lanes I and J) in 1 mM EDTA. Fragmentation products were run on a 2% TBE agarose gel with a 100 bp ladder (Lanes A, F and K).
Figure 2D:
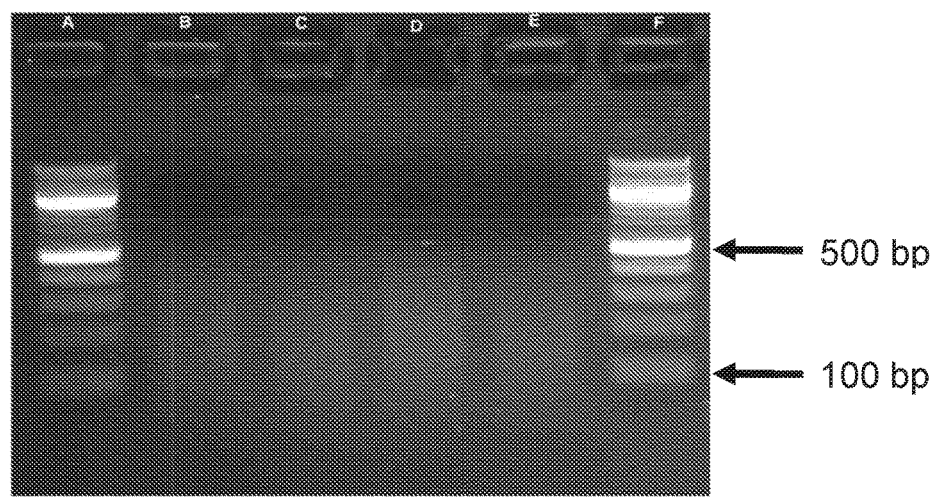
FIG. 2D shows DNA fragmentation time optimization at 42° C. for 5 minutes. Fifty ng of high molecular weight purified *E. coli* DNA was used for enzymatic reaction incubation times of: 5 min. with DNA stored 0.1 mM EDTA (Lanes B and C); or stored in 1 mM EDTA (Lanes D and E). Fragmentation products were run on a 2% TBE agarose gel with a 100 bp ladder (Lanes A and F).
Figure 2E:
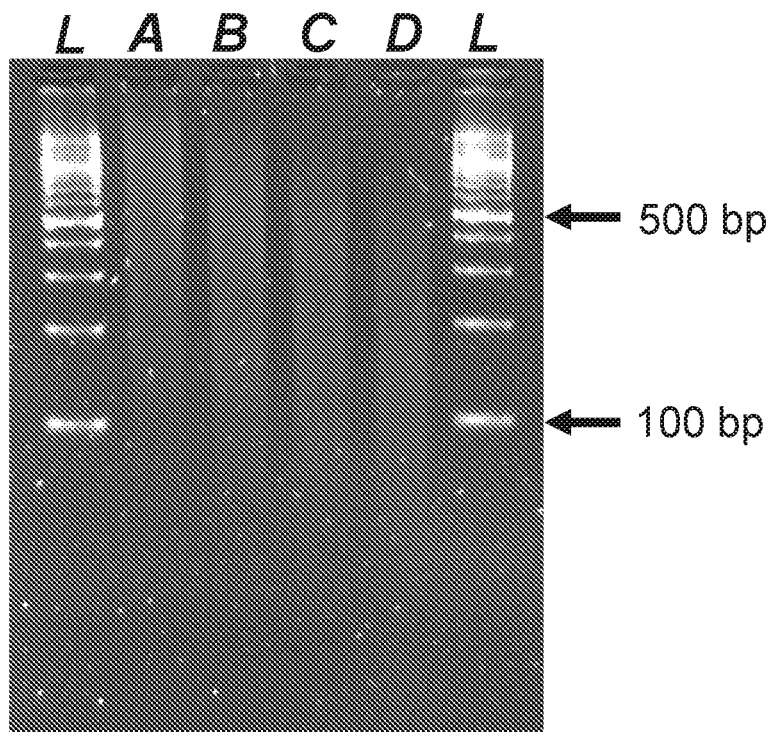
FIG. 2E shows DNA fragmentation time optimization for large DNA inserts at 37° C. from 2-5 min, 40 sec. Fifty ng of high molecular weight purified Human female DNA was used for random enzymatic fragmentation. Fragmentation products were run on a 2% TBE agarose gel with a 100 bp ladder (Lanes L). Lane A: Incubation was 2 min; Lane B: 3 min; Lane C: 4 min; and, Lane D: 5 min, 40 sec.
Figure 2F:
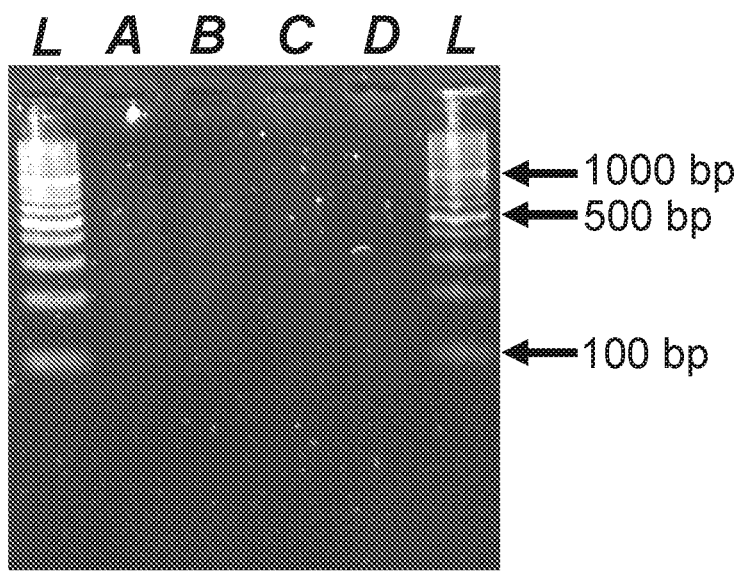
FIG. 2F shows the optimization of fragmentation of one ng Human female DNA with varied enzyme input incubated at 37° C. for 5 min, 40 sec, followed by 65° C. for 5 min. Fragmentation products were run on a 2% TBE agarose geland stained with SYBR Gold™. Lanes L: 100 bp ladder; Lane A: 0.2 µl enzyme; Lane B: 0.3 µl; Lane C: 0.4 µl; and, Lane D: 0.5 µl.
Figure 2G:
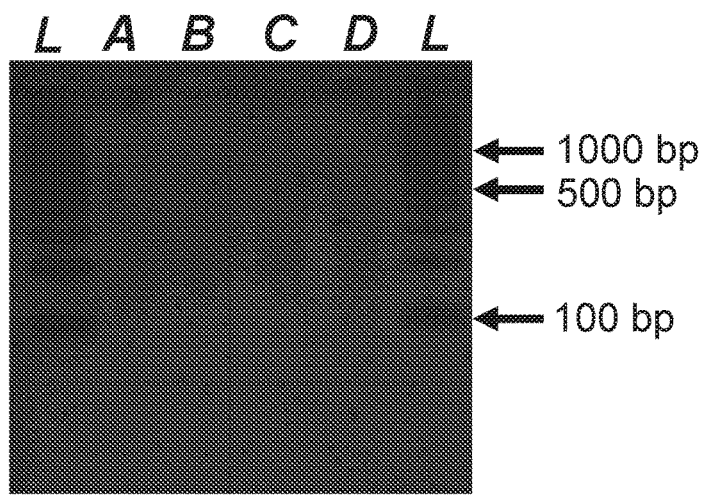
FIG. 2G shows the inverted image of FIG. 2F. Lanes L: 100 bp ladder; Lane A: 0.2 µl enzyme; Lane B: 0.3 µl; Lane C: 0.4 µl; and, Lane D: 0.5 µl.

Random enzymatic fragmentation was performed using dsDNA Shearase™ Plus (Zymo Research) according to the manufacturer's recommended conditions with the following exceptions: 1) the total reaction volume was 5 µl total; 2) the fragmentation temperature and incubation time was optimized for the desired fragmentation length distribution as shown in FIGS. 2A-E, (the samples were incubated at 42° C. for 4.5 min and heat inactivated at 65° C. for 5 min. using a thermal cycler to optimize fragmentation for 50-600 bp fragments, with the majority of the fragment length distribution located between 100-400 bp; or, 3) fragmentation temperature was held at 37° C. for 5 min, 40 sec, but enzyme volume varied in FIGS. 2F-G.

Figure 2H:
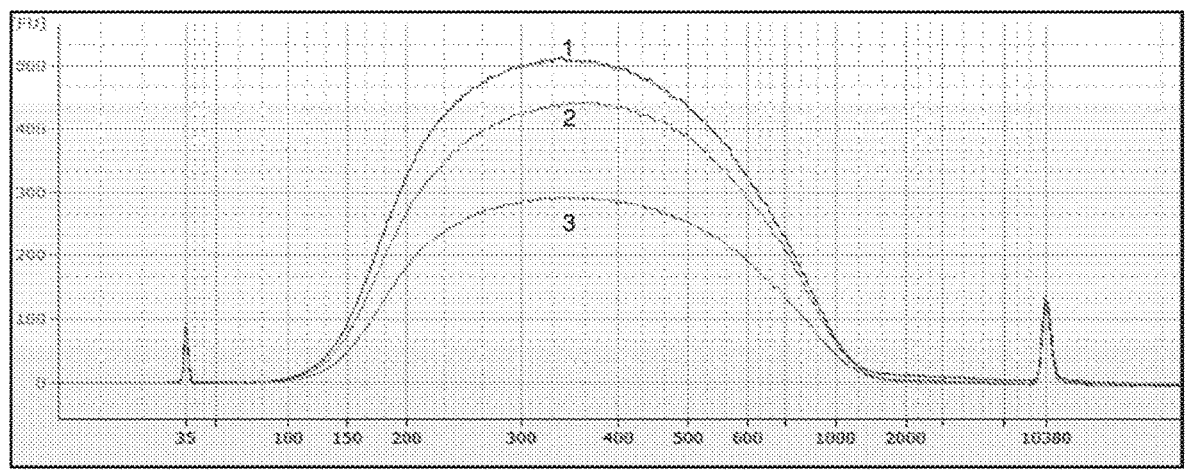
FIG. 2H shows DNA using ultrasonic fragmentation following manufacturer recommendations. Line 1: *B. pertussis*; Line 2: *E. coli*; and, Line 3: *C. difficile*.

Fragmentation of the purified *B. pertussis, E. coli,* and *C. difficile* genomic DNA by ultra-focused sonication was performed using a Covaris® Focused-ultrasonicator, according to the manufacturer's recommended conditions, to generate a fragment size distribution of about 100-1,250 bp, as shown in FIG. 2H.

Figure 3A:
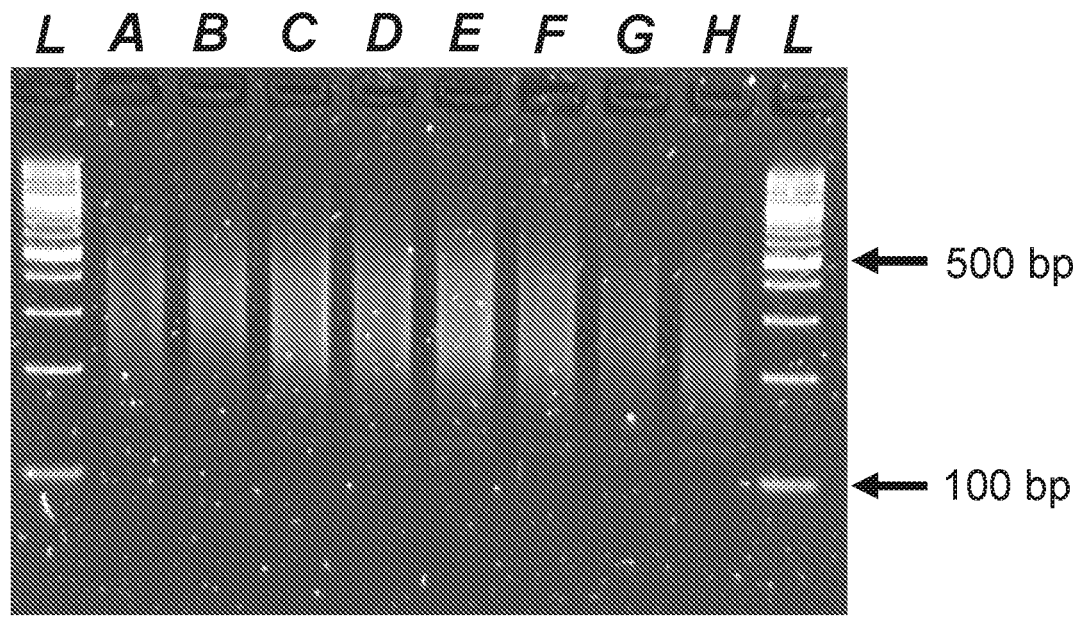
FIG. 3A shows library construction products produced from different probe hybridization temperatures ran on a 2% TBE agarose gel with 100 bp ladder (Lanes L). The reactions were performed using 50 ng of high molecular weight purified Human female DNA and was enzymatically fragmented for 5 min., 40 sec., at 37° C. Probe hybridization was performed in a thermal cycler for 1 min, 40 sec. Lane A: 4° C. probe incubation temperature; Lane B: 22° C.; Lane C: 40° C.; Lane D: 55° C.; Lane E: 64° C.; Lane F: 71° C.; Lane G: 80.4° C.; and, Lane H: 95° C. Final libraries were size selected with 0.85× Ampure™ XP beads.
Figure 3B:
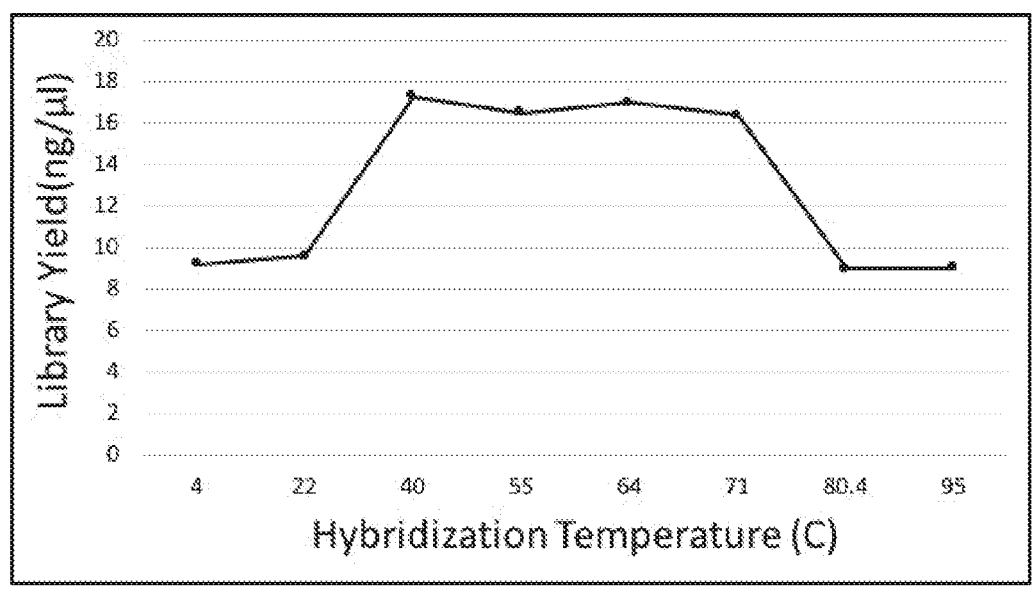
FIG. 3B plot of library construction yields from products in FIG. 3A, determined by Qubit™ fluorometer. Library yields decreased at low and high temperatures, whereas the optimal range of probe hybridization was between 40-70° C.

The enzymatic and ultrasonic fragmentation products were used directly, without additional purification, in subsequent DNA fraying and probe hybridization steps. More specifically, the DNA fraying and probe hybridization reactions were performed in buffer conditions of 10-20 mM Tris-HCl, 25-35 mM $MgCl_2$, 10-75 mM NaCl, 100 µg/ml bovine serum albumin (BSA), 1 mM dithiothreitol (DTT), 1-5 mM deoxyribonucleotide triphosphate (dNTP)s, 5-50% glycerol, and 20 mM random probe. The random probe pool was composed of oligonucleotides of 6-12 base pairs in length and the first 5' base of each probe was a cleavable base dUTP. The incubation temperature was estimated by calculating the minimal probe length with 100% GC content, and the longest probe length with 100% AT content for hybridization between temperatures of 40-70° C. Multiple hybridization/fraying temperature conditions were performed using a thermal cycler, and quantified using a Qubit® fluorometer, as shown in FIG. 3. The final reaction condition was an incubation at 55° C. for 1 min., 45 sec. At 1 min., 44 sec., the sample was removed from the thermal cycler and immediately submerged in ice water for 10-20 sec.

Next, 1.5 units of T4 DNA polymerase was added to each sample and incubated at 8° C. for 1 min., and then 12° C. for 1.5 min. in the thermal cycler. The samples were immediately removed and placed on ice until the addition of the adaptor pool.

Figure 4A:
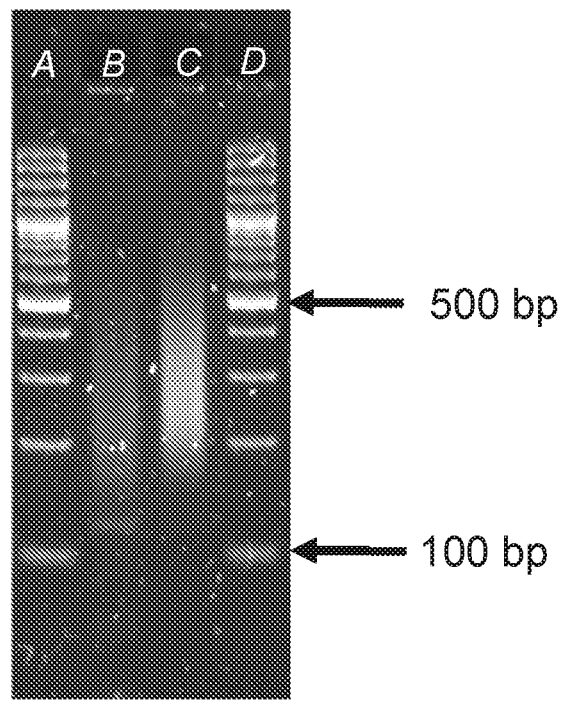
FIG. 4A shows library construction products produced using sequentially-performed T4 DNA polymerase and UDG/T4 DNA ligase reactions. The reactions were performed using 50 ng of high molecular weight purified *E. coli* DNA and was enzymatically fragmented for 5 min., 40 sec., at 37° C. Final library products were run on a 2% TBE agarose gel with a 100 bp ladder (Lanes A and D). Lane B: library was not size-selected. Lane C: library was size-selected.
Figure 4B:
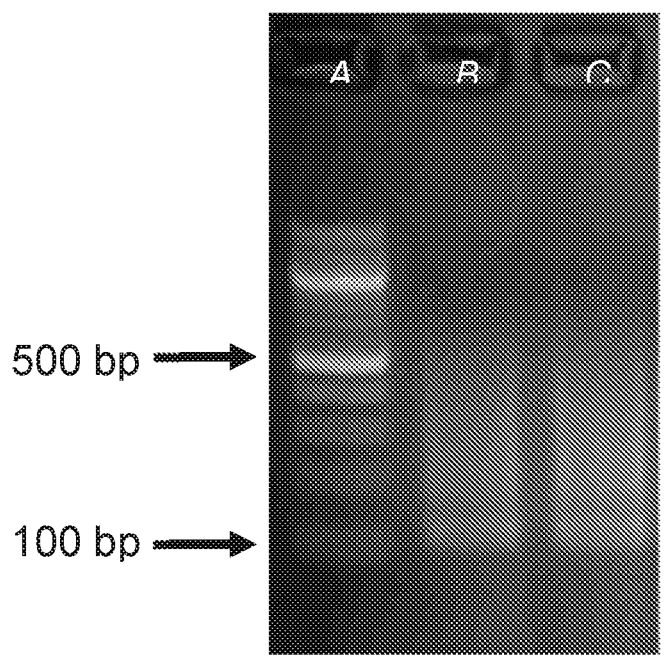
FIG. 4B shows library construction products produced using simultaneous sequentially-performed T4 DNA polymerase and UDG/T4 DNA ligase reactions. The reactions were performed using 50 ng (Lane B) or 25 ng (Lane C) of high molecular weight purified *E. coli* DNA was enzymatically fragmented for 5 min., 40 sec., at 37° C. The final library products (Lanes B and C) were not size-selected, and were run on a 2% TBE agarose gel with a 100 bp ladder (Lane A).
Figure 5:
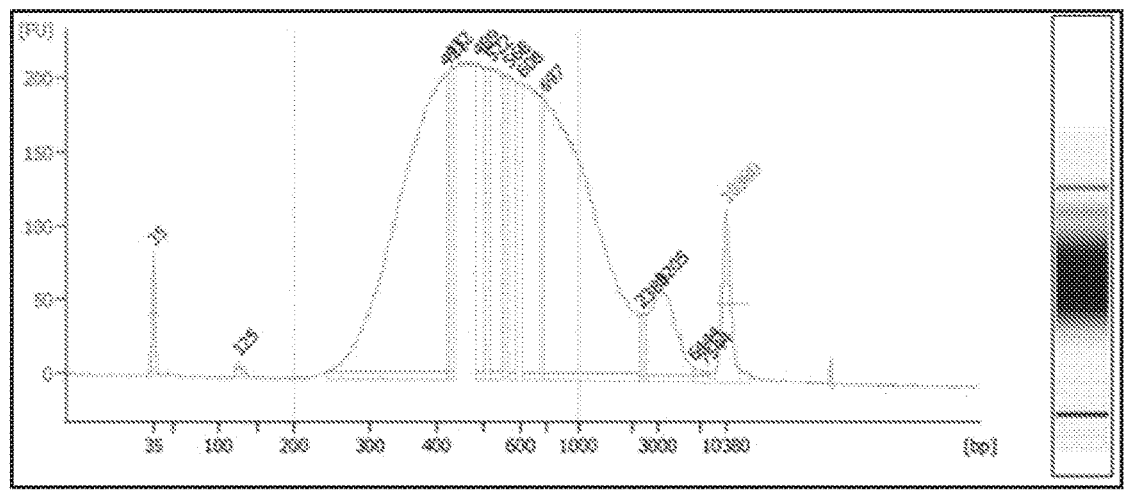
FIG. 5 shows a trace analysis of pooled bacterial libraries generated from 50 ng of purified high molecular weight DNA derived from *B. pertussis, E. coli*, and *C. difficile*. The x-axis shows the base pair length and the y-axis is the fluorescent units (FU). The libraries were generated to produce a larger library insert size, which is illustrated by the bioanalyzer fragment length distribution range of 300-1500 bp.
Figure 6:
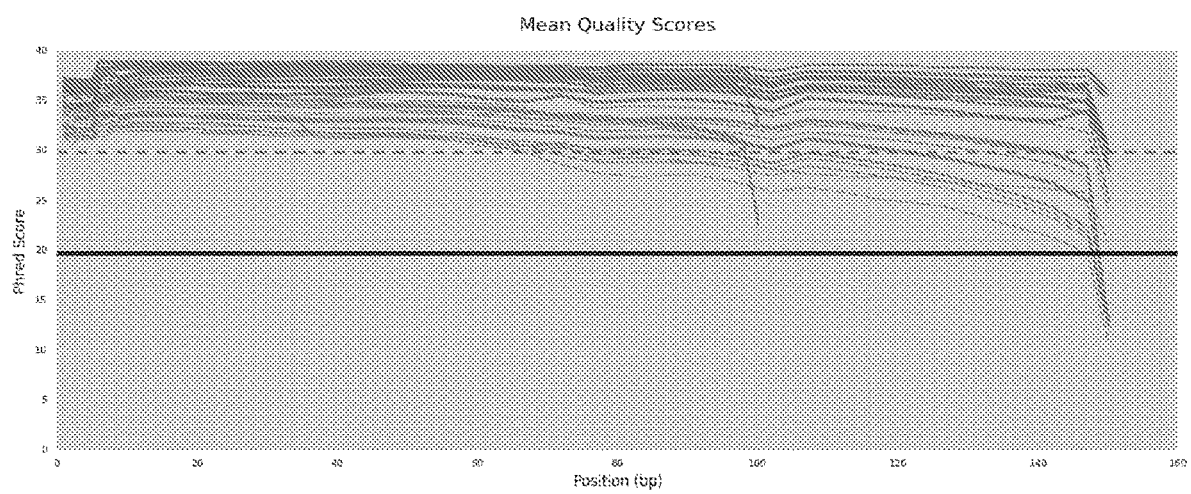
FIG. 6 shows a composite plot of the Phred mean quality scores of *B. pertussis, E. coli*, and *C. difficile* libraries sequenced on a 100 bp and 150 bp paired-end sequencing run using a HiSeq™ 2500 rapid run. Phred mean quality scores were generated using MuiltiQC. Dark grey solid lines are the first paired-end read, and the light solid lines are the second paired-end read. The light grey hash line represents a Phred score of 30 and the solid black line represents a Phred score of 20. The majority of first paired-end reads have an average score above 30. The second paired-end reads are above 30, and decrease with sequencing length to above 20. This plot also illustrates that the sequencing complexity of the libraries were high, and, therefore, did not result in low Phred scores.
Figure 7A:
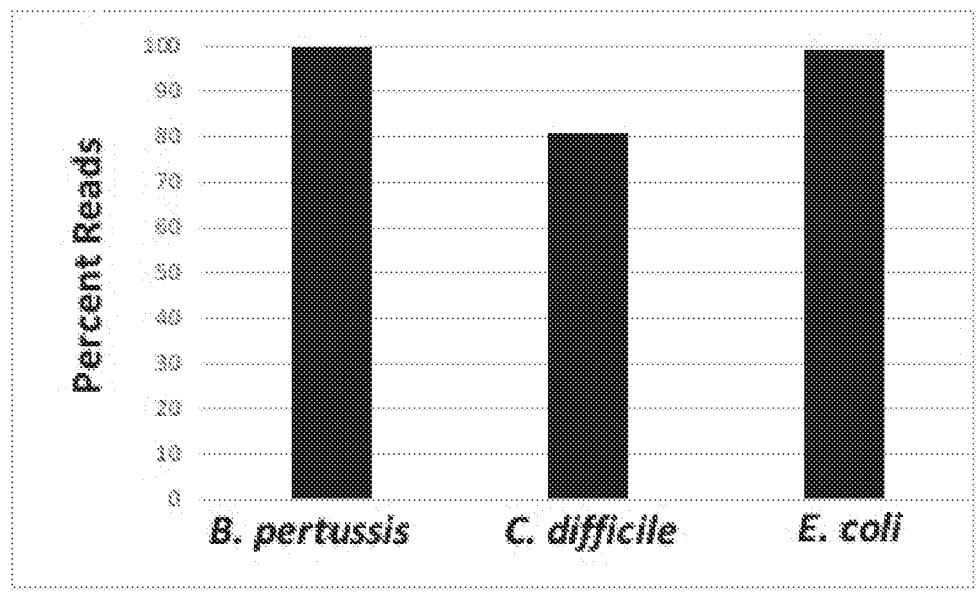
FIG. 7A shows the percentage of mapped reads per sequencing run performed with libraries produced from the genomes of *B. pertussis, E. coli*, and *C. difficile*. Greater than 99% of the reads were found to map successfully to the bacteria's respective genomes. *C. difficle* was found to have a mapping rate of approximately 81%. The remaining 19% mapped to a phage genome, and likely indicates that the original purified source DNA preparation became contaminated.
Figure 7B:
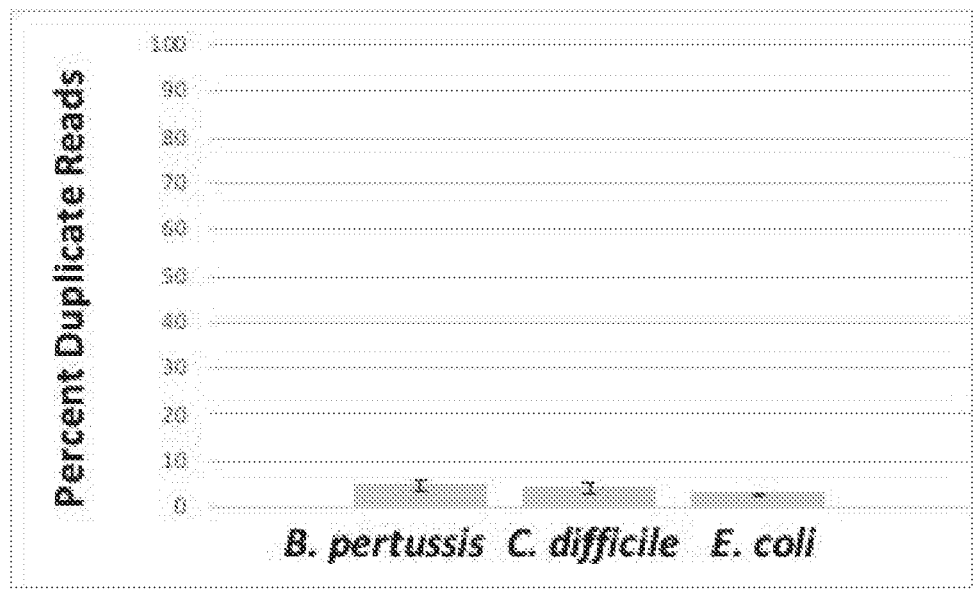
FIG. 7B shows the percentage of duplicate reads per libraries produced from the genomes of *B. pertussis, E. coli*, and *C. difficile*. The average coverage of each bacterial species was over 250× and was found to produce 1-4% duplicate reads between samples.
Figure 8:
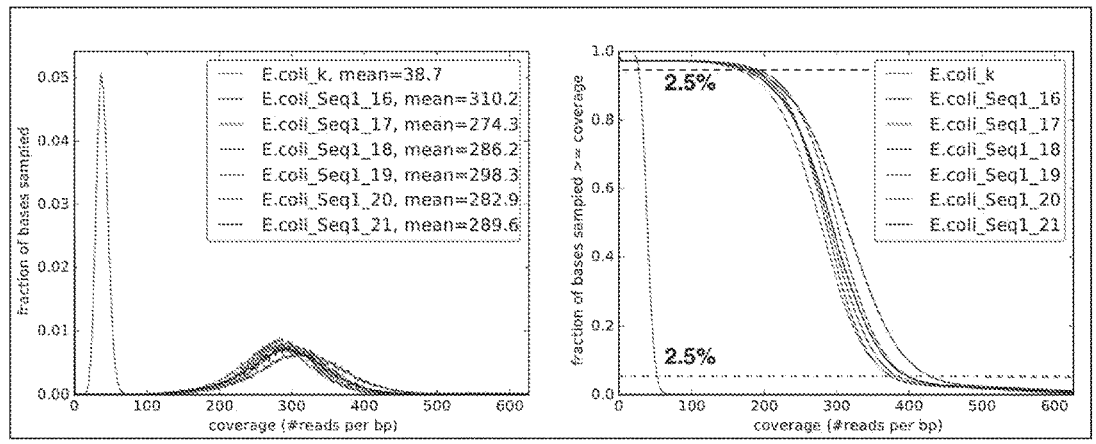
FIG. 8 shows that *E. coli* mapping coverage across multiple replicates in libraries generated from random fragments that were produced either enzymatically or ultrasonically. The top left panel plot x-axis is the coverage (number of reads per base pair) and y-axis is the fraction of bases sampled. The left panel shows the average coverage per replicate using random enzymatic fragmentation (dark solid lines) versus ultrasonic fragmentation (light grey line). The random fragmentation samples show broad coverage of bases around the mean, while the ultrasonic sample shows that each base is covered with a similar depth of coverage. The right panel plot x-axis is the coverage (number of reads per base pair) and y-axis is the fraction of bases sampled greater than or equal to the depth of coverage. The right panel plot illustrates the percentage of genome bases that are represented by high or low coverage. With random enzymatic fragmentation, regions of the genome are represented with high and low coverage, but is, overall, representative of less than 5% of the genome, while genome coverage with ultrasonic fragmentation was nearly uniform.
Figure 9:
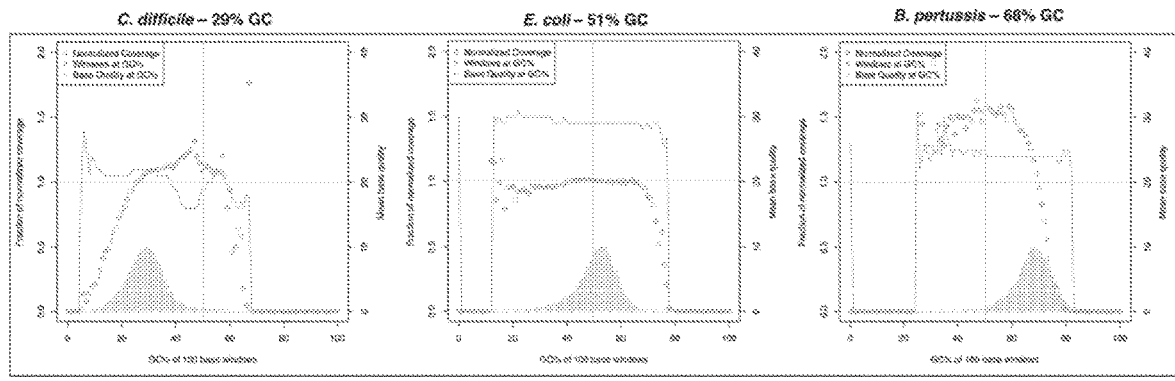
FIG. 9 shows sequencing GC bias among libraries generated from the genomes of *C. difficile, E. coli*, and *B. pertussis*. The GC contents in *C. difficile, E. coli*, and *B. pertussis* libraries was 29%, 51%, and 68%, respectively. In the FIG., the x-axis (vertical bars) is the percent GC content of 100 base windows across the genome of the three bacterial species. The left y-axis is the fraction of normalized coverage (circles) and the right y-axis is the mean base quality score (solid line). A normalized value of 1 is ideal (circles) and is observed in the *E. coli* plot.

The adaptor pool was a stock Illumina® adaptor pool containing truncated adaptors with phosphorothioate modifications on the last 3' bases of each oligonucleotide. The 45 µM stock adaptor pool concentration was diluted to a working concentration of 0.75 µM, and stored on ice until its addition to the reaction mixture. One µl of an adaptor pool working concentration was added to each sample, followed by the addition of ligation buffer (291.2 mM Tris-HCl, 44.1 mM $MgCl_2$, 4.4 mM DTT, 4.4 mM adenosine triphosphate (ATP), 26.47% polyethylene glycol (PEG)-6000, 1.5 units of Uracil DNA Glycosylase (UDG), and 1,000,000 units of T4 DNA ligase. The reaction mixture was vortexed and placed in the thermal cycler under the following conditions: 1) 8° C. for 30 sec.; 2) 12° C. for 30 sec.; 3) 20° C. for 30 sec; 4) 25° C. for 4 min.; 5) 35° C. for 4 min; and, 6) held at 4° C. The adaptor pool contained adaptors with a 3' T-overhang for T/A ligation, and blunted adaptors for blunt end ligation. The adaptors were ligated to the probe-template complex in the same reaction that base cleavage was performed. The T4 DNA polymerase reaction and the UDG/T4 DNA Ligase reactions were performed sequentially, meaning the addition of polymerase preceded the addition of ligase and UDG, (FIG. 4A), as well as simultaneously, (polymerase, ligase, and UDG are added at the same time), in the same tube (FIG. 4B) to produce libraries for NGS. The simultaneous reaction was placed in a thermal cycler under the following conditions: 1) 8° C. for 1 min.; 2) 12° C. for 2 min., 30 sec.; 3) 20° C. for 30 sec; 4) 25° C. for 4 min.; 5) 35° C. for 4 min; and, 6) held at 4° C. Irrespective of whether the polymerase and UDG/ligase enzymes were added sequentially or simultaneously, respective buffers for the enzymes were always present at the time template fragments were added.

In preparation for a sequencing reaction, the samples were removed from the thermal cycler and used directly in a PCR reaction. The 30 µl PCR reaction contained the appropriate PCR probes for amplification of the library, using 2 units of Thermo Scientific Phusion® polymerase, 1×HF buffer, and 200 µM dNTPs. Post-PCR, the samples were sized selected with Ampure XP® beads to the desired library fragment size range of 300 to 800 bp. Pre- and post-sequencing quality control was performed on the libraries using an Agilent BioAnalyzer® 2100 and using a MultiQC® toolbox (Ewels et al. Bioinformatics 2016) to generate mean Phred scores. See FIGS. 5-9. Sequencing was performed using an Illumina® HiSeq 2500 rapid run. In the case of high and low GC content genomes, minimal read drop out occurred at the high and low GC content extremes in *C. difficile* and *B. pertussis*. The results are comparable to other library construction methods.

Figure 10A:
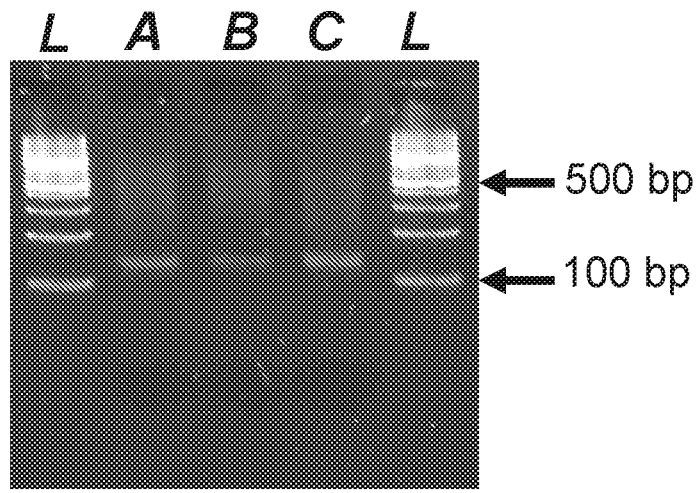
FIG. 10A shows successful low input library construction. One ng of high molecular weight purified Human female DNA was enzymatically fragmented for 5 min., 40 sec. at 37° C. The volume of enzyme varied between lanes during the fragmentation step of library construction. The library construction products were Ampure XP bead purified, but not size selected. The libraries were run on a 2% TBE agarose gel with a 100 bp ladder (Lanes L). Lane A: 0.3 µl enzyme input; Lane B: 0.4 µl; and, Lane C: 0.5 µl.

Example 2. Rapid Next Generation Sequencing Library Construction with Random Probes Containing a 5' Cleavable End Using Low and Ultra Low Input DNA To test low input potential for library construction, fragmentation was optimized for one ng of high molecular weight Human female DNA and was enzymatically fragmented with varied volumes of enzyme input and incubated 37° C. for 5 min, 40 sec., followed by 65° C. for 5 min. FIGS. 2F-G show the optimization of one ng fragmentation and illustrates the potential to generate libraries with short or long inserts. FIG. 10A shows the libraries generated under the aforementioned fragmentation conditions following the Example one sequential conditions.

Figure 10B:
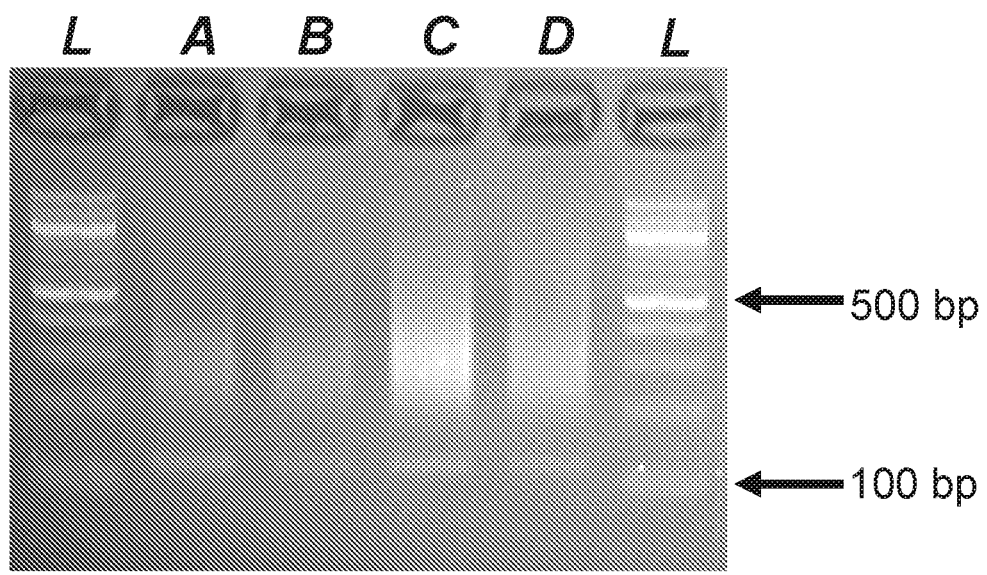
FIG. 10B shows successful ultra low input library construction. Fifty ng of high molecular weight purified *E. coli* DNA was enzymatically fragmented for 5 min., 40 sec. at 37° C. The fragmentation products were diluted to 0.5 ng/µl (Lanes A and B) and 1.0 ng/µl (Lanes C and D) concentrations in fragmentation buffer. The dilutions were used for library construction as described in Example 1. The library construction products were not size selected, and were run on a 2% TBE agarose gel with a 100 bp ladder (Lane L).
Figure 10C:
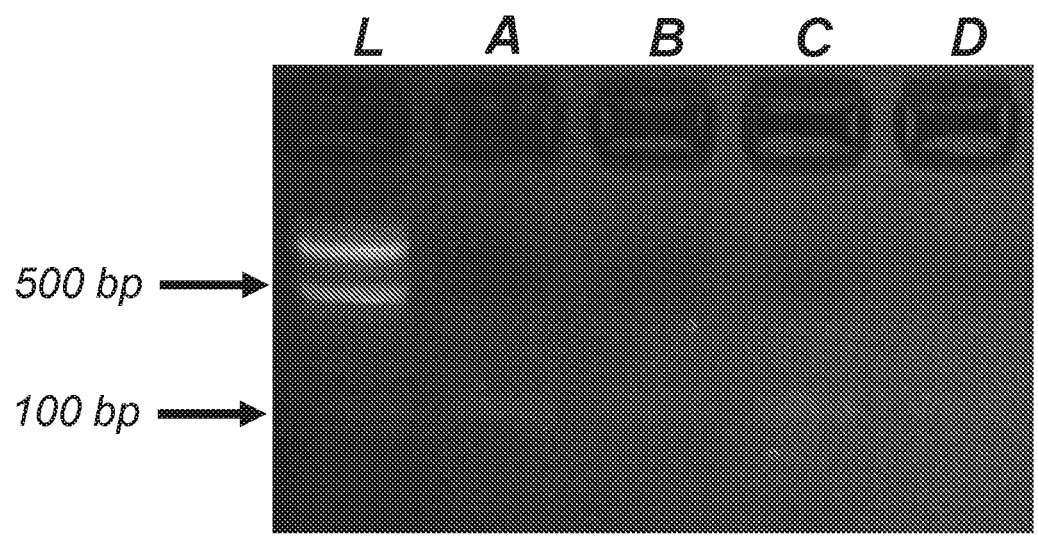
FIG. 10C shows successful ultra low input library construction. Fifty ng of high molecular weight purified *E. coli* DNA was enzymatically fragmented for 5 min., 40 sec. at 37° C. The fragmentation products were diluted to 50 pg/µl (Lanes A and B) and 100 pg/µl (Lanes C and D) concentrations in fragmentation buffer. The dilutions were used for library construction as described in Example 1. The library construction products were not size selected, and were run on a 2% TBE agarose gel with a 100 bp ladder (Lane L).

Libraries to test ultra low input potential for library construction were generated from 50 ng high molecular weight *E. coli* DNA that was enzymatically fragmented at 37° C. for 5 min, 40 sec., followed by heat inactivation of the enzyme at 65° C. for 5 min. The fragmented DNA was diluted to 1 ng, 0.5 ng, 100 pg, and 50 pg in fragmentation buffer for library construction as described in Example 1. FIGS. 10B-C show that the library construction protocol works for ultra low input DNA down to at least 50 pg.

Figure 11A:
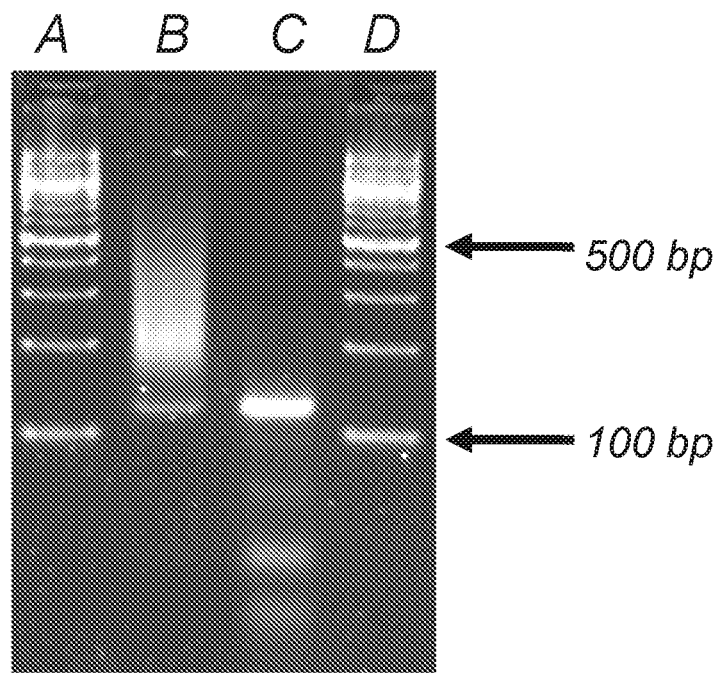
FIG. 11A shows successful library construction using hybridization probes containing 5' and 3' cleavable bases and using sequentially-performed T4 DNA polymerase and UDG/T4 DNA ligase reactions. The library was generated using 50 ng of high molecular weight purified *E. coli* DNA that was fragmented for 5 min., 40 sec. at 37° C. (Lane B). A negative control was run in which DNA input was not provided for the fragmentation (Lane C). All reactions were performed in a single tube without purification between steps.
Figure 11B:
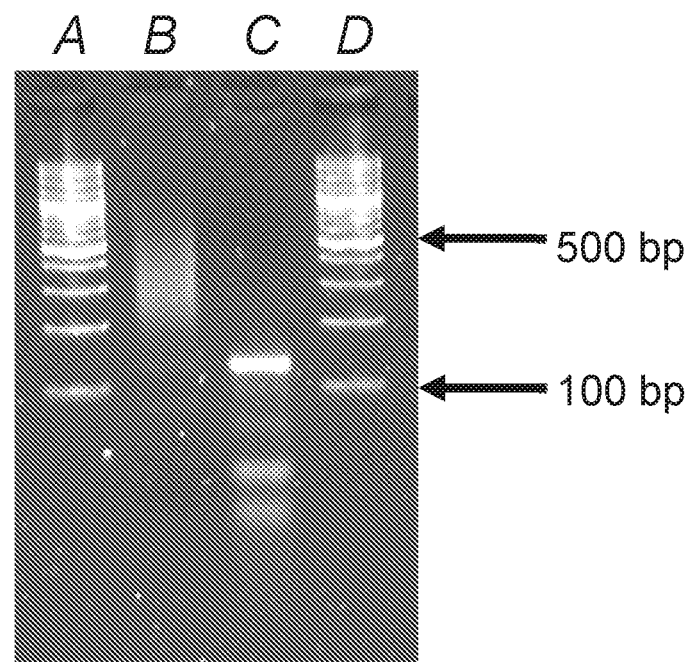
FIG. 11B shows successful library construction using hybridization probes containing 5' and 3' cleavable bases and using simultaneous sequentially-performed T4 DNA polymerase and UDG/T4 DNA ligase reactions. The library was generated using 50 ng of high molecular weight purified *E. coli* DNA that was fragmented for 5 min., 40 sec. at 37° C. (Lane B). A negative control was run in which DNA input was not provided for the fragmentation (Lane C). All reactions were performed in a single tube without purification between steps.
Figure 12:
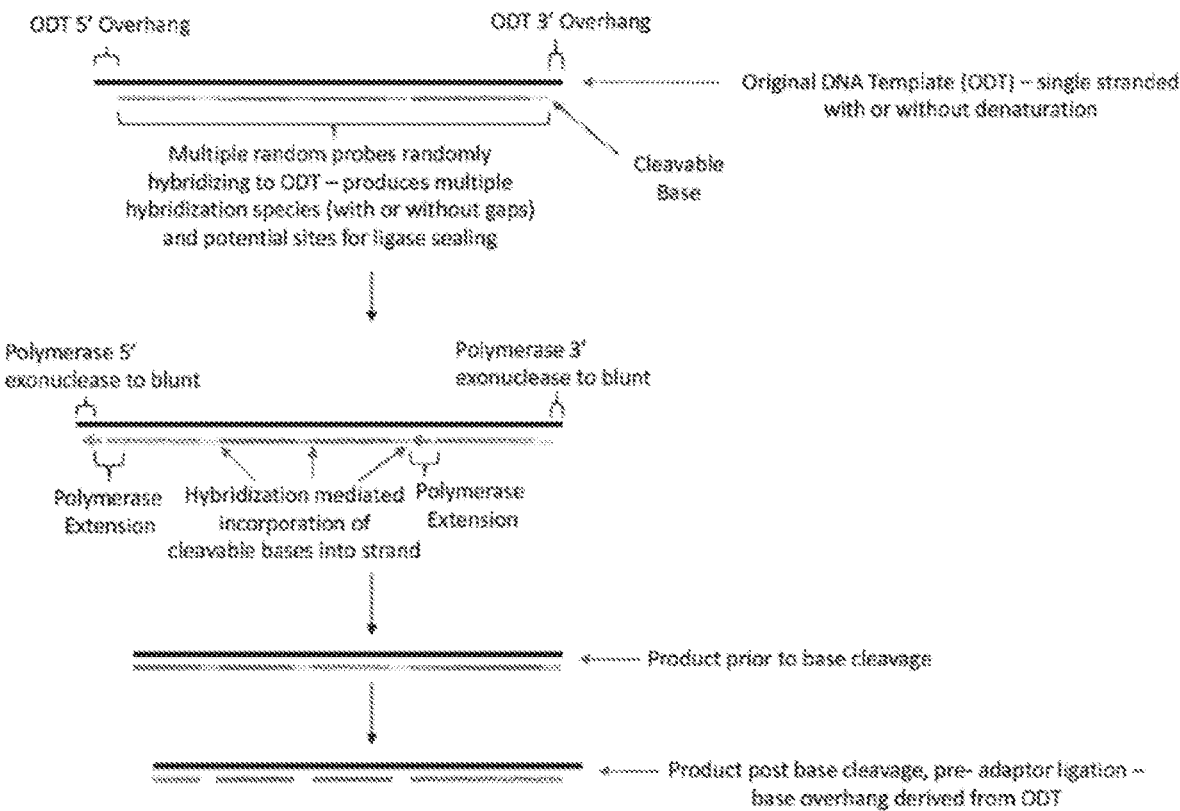
FIG. 12 depicts an alternative method in which single-stranded DNA is used as the original DNA template. The single-stranded original DNA template (shown as a black line) can be used with or without denaturation. In this method, multiple random probes randomly hybridize to the original DNA template and produce multiple hybridization species (with or without gaps) and potential sites for ligase sealing.

Example 3. Rapid Library Construction Using Hybridization Probes Containing 5' and 3' Cleavable Bases A library in which the hybridized probes contained 5' and 3' cleavable bases was generated using 50 ng of high molecular weight purified *E. coli* DNA that was enzymatically fragmented for 5 min., 40 sec. at 37° C. T4 Polymerase and T4 ligase steps were carried out as described in Example 1, the following exceptions: 1) the probe contained a 5' cleavable base (rATP) and a 3' cleavable base (rUTP); and, 2) UDG was replace with 1.5 units of RNAse H. The resulting library was generated to the expected fragment length distribution. After a bead purification step, the library was run on a 2% agarose gel and stained with SYBR Safe™ (FIG. 11A-B, sequential and simultaneous, respectively). The agarose gel also shows absence of any library products in a second library preparation that was generated as a negative control without DNA input for fragmentation.

REFERENCES

Ewels Philip, Magnusson Måns, Lundin Sverker, and Käller. MultiQC: *Summarize analysis results for multiple tools and samples in a single report*. Bioinformatics (2016). DOI: 10.1093/bioinformatics/btw354. PMID: 27312411.

What is claimed is:

1. A method for preparing a high-throughput sequencing library comprising the steps of:
   A. generating double-stranded fragments from a plurality of polynucleotides;
   B. fraying the ends of the fragments to expose single-stranded regions;
   C. hybridizing oligonucleotide probes to the single-strand regions to form double-stranded duplexes, wherein the probes comprise a cleavable:
      (1) 5' chemically active group;
      (2) 3' chemically active group; or
      (3) 5' and 3' chemically active groups;
   wherein the lengths of the probes are at least equivalent to the exposed single-stranded regions of the frayed fragments;
   D. contacting the double-stranded duplexes with at least one cleaving agent to cleave the chemically active group, or groups, to produce a single-stranded 3' overhang, a single-stranded 5' overhang, or single-stranded 3' and 5' overhangs in the double-stranded duplexes; and
   E. ligating at least two sets of double-stranded DNA adaptors to the double-stranded duplexes, wherein
      (1) the adaptors in a first set of adaptors comprise at least one of the following:
         i. a 3' overhang complementary to the overhang end of the 3' single-stranded overhang of the double-stranded duplex, if present; or
         ii. a 5' overhang complementary to the overhang end of the 5' single-stranded overhang of the double-stranded duplex, if present, and
      (2) the adaptors in a second set of adaptors comprise at least one of the following:
         i. a 3' overhang complementary to the overhang end of the 3' single-stranded overhang of the double-stranded duplex, if present;
         ii. a 5' overhang complementary to the overhang end of the 5' single-stranded overhang of the double-stranded duplex, if present; or
         iii. a blunt end to ligate to the blunt end of the double-stranded duplex, if present.

2. The method for preparing a high-throughput sequencing library according to claim 1,
   wherein: the probes comprise a 5' chemically-active group;
   the at least one cleaving agent cleaves the 5' chemically active group;
   the adaptors in the first set of adaptors comprise a 3' overhang complementary to the overhang end of the 3' single-stranded overhang of the double-stranded duplex; and
   the second set of adaptors comprise a blunt end to ligate to the blunt end of the double-stranded duplex.

3. The method for preparing a high-throughput sequencing library according to claim 1,
   wherein: the probes comprise a 3' chemically-active group;
   the at least one cleaving agent cleaves the 3' chemically active group;
   the adaptors in the first set of adaptors comprise a 5' overhang complementary to the overhang end of the 5' single-stranded overhang of the double-stranded duplex; and
   the second set of adaptors comprise a blunt end to ligate to the blunt end of the double-stranded duplex.

4. The method for preparing a high-throughput sequencing library according to claim 1,
   wherein: the probes comprise 3' and 5' chemically active groups;
   at least one cleaving agent cleaves the 3' chemically active group, and at least one cleaving agent cleaves the 5' chemically active group;
   the adaptors in the first set of adaptors comprise a 5' overhang complementary to the overhang end of the 5' single-stranded overhang of the double-stranded duplex; and
   the second set of adaptors comprise a 3' overhang complementary to the overhang end of the 3' single-stranded overhang of the double-stranded duplex.

5. The method according to claim 1, wherein the polynucleotide fragments are generated randomly, enzymatically, or by ultrasonic fragmentation.

6. The method according to claim 5, wherein the double-stranded polynucleotide fragments are 50-1000 base pairs (bp) long or 100-800 bp long.

7. The method according to claim 1, wherein the exposed single-strand region of the frayed fragment is 6-12 nucleotides in length.

8. The method according to claim 1, wherein the oligonucleotide probes comprise:
   deoxynucleotides (dNTPs); dNTP/ribonucleotide triphosphates (rNTP) hybrids; peptide nucleic acids (PNA); locked nucleic acids (LNAs); isoguanosine (isoG); isocytosine (isoC); or any combination thereof.

9. The method according to claim 1, wherein the oligonucleotide probes comprise phosphorothioate bonds.

10. The method according to claim 1, wherein the oligonucleotide probes comprise phosphorothioate modifications at one or more bases between bases 2-5 at the 3' or 5' ends, or both.

11. The method according to claim 1, wherein the oligonucleotide probes are 6-12 nucleotides in length.

12. The method according to claim 1, wherein the 5' chemically active group is selected from dUTP, rATP, rCTP, rGTP, rUTP, isoG, isoC, a methylated nucleotide, an LNA, and an PNA.

13. The method according to claim 1, wherein the 3' chemically active group is selected from dUTP, rATP, rCTP, rGTP, rUTP, isoG, isoC, a methylated nucleotide, an LNA, and an PNA.

14. The method according to claim 13, wherein the 3' chemically active group is dUTP, rATP, rCTP, rGTP, or rUTP.

15. The method according to claim 1, wherein the cleaving agent is uracil DNA glycosylase (UDG) or RNAse H.

16. A kit for preparing a high-throughput sequencing library from a plurality of double-stranded polynucleotide fragments comprising:
   1) a pool of random probes comprising a cleavable 5' chemically active group, a cleavable 3' chemically active group, or both;
   2) a pool of double-stranded truncated or full-length next generation sequencing adaptors;
   3) one or more buffers appropriate for performing the following reactions:
      (a) an enzymatic reaction to fray the ends of input polynucleotide fragments to expose single-stranded regions;
      (b) for hybridizing the probes to the single-stranded regions of the fragments to form double-stranded duplexes;

(c) an enzymatic reaction for blunting the ends of the probe/input fragment duplexes;

(d) an enzymatic reaction for cleaving the 5' or 3' ends of probes that comprise cleavable chemically active groups; and (e) an enzymatic reaction ligating the sequencing adaptors to the double-stranded duplexes.

17. The kit according to claim 16, wherein the adaptor pool comprises adaptors with a 3' overhang and adaptors with blunt ends.

18. The kit according to claim 16, wherein the adaptor pool comprises adaptors with a 5' overhang and adaptors with blunt ends.

19. The kit according to claim 16, wherein the adaptor pool comprises adaptors with a 5' overhang and adaptors with a 3' overhang.

20. The kit according to claim 16, comprising adaptors with a phosphorothioate modification on the last 1-3 bases of the 3', 5', or both, ends.

* * * * *